(12) United States Patent
Giancola

(10) Patent No.: US 9,504,505 B2
(45) Date of Patent: Nov. 29, 2016

(54) DEVICE FOR SELECTIVE BIOLOGICAL SYNTHESIS OF A BONE TISSUE

(75) Inventor: Rinaldo Giancola, Milan (IT)

(73) Assignee: 4ELDER S.R.L., Milan (IT)

( * ) Notice: Subject to any disclaimer, the term of this patent is extended or adjusted under 35 U.S.C. 154(b) by 271 days.

(21) Appl. No.: 13/704,469

(22) PCT Filed: Jun. 15, 2011

(86) PCT No.: PCT/IB2011/052603
§ 371 (c)(1),
(2), (4) Date: Feb. 22, 2013

(87) PCT Pub. No.: WO2011/158193
PCT Pub. Date: Dec. 22, 2011

(65) Prior Publication Data
US 2013/0144344 A1 Jun. 6, 2013

(30) Foreign Application Priority Data

Jun. 15, 2010 (IT) .............................. VR2010A0121

(51) Int. Cl.
| | | |
|---|---|---|
| A61B 17/04 | (2006.01) | |
| A61B 17/84 | (2006.01) | |
| A61F 2/08 | (2006.01) | |
| A61B 17/86 | (2006.01) | |
| A61B 17/70 | (2006.01) | |
| A61B 17/74 | (2006.01) | |
| A61B 17/88 | (2006.01) | |

(52) U.S. Cl.
CPC ......... *A61B 17/864* (2013.01); *A61B 17/7098* (2013.01); *A61B 17/742* (2013.01); *A61B 17/8805* (2013.01)

(58) Field of Classification Search
USPC ...................................................... 606/93, 92
See application file for complete search history.

(56) References Cited

U.S. PATENT DOCUMENTS

| | | | |
|---|---|---|---|
| 6,048,343 A | 4/2000 | Mathis et al. | |
| 7,717,947 B1 * | 5/2010 | Wilberg et al. | ............... 606/304 |
| 2004/0267265 A1 | 12/2004 | Kyle | |
| 2007/0233123 A1 * | 10/2007 | Ahmad | ................ A61B 17/863 |
| | | | 606/307 |
| 2008/0249530 A1 * | 10/2008 | Truckai et al. | .................. 606/94 |
| 2010/0106199 A1 * | 4/2010 | Sawa et al. | .................... 606/304 |

FOREIGN PATENT DOCUMENTS

| | | |
|---|---|---|
| DE | 20317120 | 4/2004 |
| WO | WO2006070961 | 7/2006 |
| WO | WO2007005614 | 1/2007 |
| WO | WO2007106774 | 9/2007 |
| WO | WO2009063524 | 5/2009 |

* cited by examiner

*Primary Examiner* — Sameh Boles
(74) *Attorney, Agent, or Firm* — Tutunjian & Bitetto, P.C.

(57) ABSTRACT

Device for selective biological synthesis of a bone tissue including a screw for the stabilization of a fracture or of a porotic bone tissue, wherein said screw is arranged along an axis (X), substantially longitudinal with respect to said screw, and it is constituted by an extended body, from a first end or tip and from a second end or head, wherein at least said extended body and said second end or head include a longitudinal channel, wherein said extended body has at least one hole or slot, wherein said device includes a pin inserted into the longitudinal channel and provided with means for releasable connection with said screw, for reinforcing the device and for the releasable closure thereof.

18 Claims, 3 Drawing Sheets

DEVICE FOR SELECTIVE BIOLOGICAL SYNTHESIS OF A BONE TISSUE

TECHNICAL FIELD OF THE INVENTION

The present invention regards a device for selective biological synthesis of a bone tissue indicated for the stabilization of bone fractures, in particular for the subcapital pertrochanteric bone fractures of the femur and/or other bone regions, and for carrying, in the bone tissue, biological substances or bone cement useful for the primary stabilization and/or regeneration of the bone tissue.

DESCRIPTION OF RELATED ART

In the field of orthopedics, in particular traumatology, there are known some devices which allow, by injecting bone cement into the site of intervention, stabilizing possible bone fractures generated by a trauma or by an osteoporotic tissue, especially in old female patients, particularly affected by such condition. Actually, such patients are those in which the low level of bone stability does not guarantee satisfactory stabilization results through conventional osteosynthesis means. For example, patent application WO 2009063524 on behalf of the applicant, describes a screw for stabilizing a bone fracture, comprising a longitudinal hollow body provided, in the lateral surface thereof, with through holes through which the passage of bone cement or other active substances that can be introduced through the head of the screw is allowed.

The United States patent U.S. Pat. No. 6,048,343 has a system of bone screws comprising a cannulated screw, provided with apertures, and an adapter suitable to be reversibly coupled to the screw and to means for injecting the bone cement or a suitable composition. However, such systems have the disadvantage lying in the fact that the fluids introduced into the screw, due to the physical laws that regulate the passage thereof, flow out through the holes most proximal to the inlet, complicating reaching the farthest holes, especially in cases of high viscosity fluids, such as the bone cement. Due to such reason, the stabilization of the fractures or of a porous bone tissue obtained through such known devices is complex and not entirely efficient.

In the German utility model DE 20317120 (U1) there is described a bone screw, in particular a pedicle screw, having a threaded shank provided with a through aperture in the longitudinal direction for the introduction of a guide wire, the screw also comprises an arrangement for at least partly fixing a stiffening insertable device into the aperture.

From the United States patent U.S. Pat. No. 6,048,343 (A) there is known a bone screw system comprising a cannulated bone screw and an adapter to be releasably coupled with the screw. The screw has a head provided with an aperture and a shank provided with a blind hole in communication with the aperture of the head. The screw has a threaded portion which has a plurality of apertures on the core of the threading. The adapter has a distal end adapted for the resolvable coupling with the head and it has a passage which is extended longitudinally therethrough for the communication with the hole of the screw. The adapter further comprises a gripping portion having a plurality of annular crests spaced from each other. The proximal end of the adapter has a clutch for the coupling with a device for supplying, through the adapter and the hole through the apertures on the core of the threading, an adhesive composition for increasing the grip of the threads.

In the United States patent application US 2007/233123 (A1) there is described a bone fixing device comprising an extended shaft provided with a first and a second end, the first end generally being opposite to the second. The extended shaft defines a longitudinal hollow hole and at least one aperture passing from the longitudinal hollow hole through a lateral wall of the extended shaft. The fixing device also comprises a threaded section proximal to the first end.

SUMMARY OF THE INVENTION

An object of the present invention is to improve the state of the prior art.

A further object of the present invention is to provide a device for selective biological synthesis of a bone tissue capable of allowing reinforcing the bone tissue located in the introduction site awaiting possible regeneration and/or consolidation thereof.

A further object of the present invention is to provide a device for selective biological synthesis of a bone tissue capable of allowing introducing various substances, such as biological fluids, fluids with variable viscosity, bone cements of various compositions, polymethylmethacrylate (PMMA), etcetera.

According to an aspect of the present invention, these objects are attained by a device for selective biological synthesis of a bone tissue as specified herein.

BRIEF DESCRIPTION OF THE DRAWINGS

Further characteristics and advantages of the invention shall be more apparent from the detailed description of a device for selective biological synthesis of a bone tissue, illustrated by way of non-limiting example, in the attached drawings wherein.

DETAILED DESCRIPTION OF EMBODIMENTS

Figure 1:
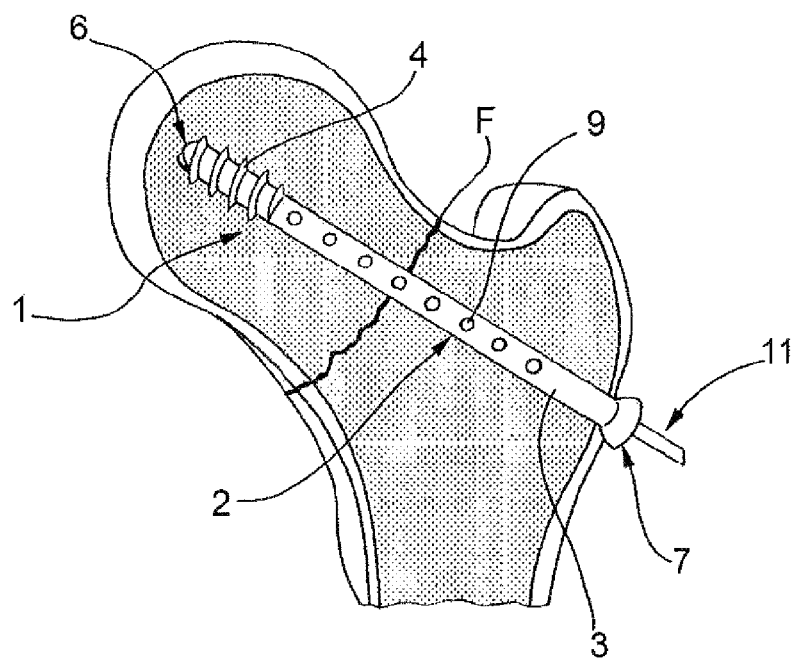
FIG. 1 is a perspective view of a device for selective biological synthesis of a bone tissue in the insertion site.

With reference to the figures, a device for selective biological synthesis of a bone tissue according to the present invention is indicated with 1. Such device is biocompatible with the tissue into which it is inserted.

The device 1 comprises a screw 2 for the stabilization of a fracture or of osteoporotic bone tissue, provided with a longitudinal axis X and comprising an extended body 3 which externally has a threading 4.

Such threading 4 is substantially arranged at the front part of the screw 2.

The extended body 3 internally comprises a longitudinal channel 5. The longitudinal channel 5 and the extended body 3 are also arranged along the axis X of the screw 2.

The screw 2 has, at the front part thereof, a first end or tip 6, substantially tapered and/or with a suitable shape capable of allowing the insertion thereof into the soft tissue, first, and bone tissue, then, of the patient. The first end or tip 6 has, as observable in FIGS. 2 and 3, a groove 12 which allows a better insertion of the screw 2 into the tissues which it should traverse.

The screw 2 also has a second end or head 7, also traversed by the longitudinal channel 5. The longitudinal channel 5 traverses at least the extended body 3 and the second end or head 7 of the screw 2; the first end or tip 6 of the screw 2 can be traversed or not traversed by the longitudinal channel 5.

The second end or head 7 has a coupling element, for example hexagonal shaped or generally of any suitable shape, capable of allowing the coupling of the screw 2 using an insertion tool, as explained hereinafter. The coupling element can be positioned in a seat recessed or projecting with respect to the second end or head 7 of the screw 2.

The screw 2 can be in form of a pin or any other means suitable for the purpose and it has a cylindrical section, prismatic section or any other shape capable of allowing the insertion thereof into the human body.

The device 1 is adapted to be coupled with an injection system S, illustrated in FIG. 6, through coupling means A of the known type and through an injector 11, as explained hereinafter in the present description. Through the injection system S and the device 1 there occurs the injection, in the site of interest, of bone cement, for example containing polymethylmethacrylate, and/or of regenerative factors, for example stem cells, growth factors, platelet gel, etcetera, and/or of other antibiotic or medicinal substances, etcetera, so as to stabilize, cure and possibly regenerate, the fractures of the patients who have suffered a trauma or osteoporotic patients.

The screws 2 are available in various dimensions, with a diameter between 6 mm to 12 mm and a length from 70 mm to 120 mm. For example, the main dimensions of the screw 2 are: diameter of 8.5 mm or 10 mm, length of 80 mm, 90 mm, 100 mm according to the anatomic needs of the patient into whom they are to be inserted. Advantageously, the previously mentioned dimensions allow providing a device for selective biological synthesis of a bone tissue that is less invasive to conserve the bone tissue and, simultaneously, mechanically suitable for the purpose.

Actually, the aforementioned dimensions were reduced with respect to the known devices, to guarantee the introduction through percutaneous access of the device 1. However, other dimensions can be used, without departing from the scope of protection of the present invention.

As observable in FIG. 1, the extended body 3 has an outer surface substantially smooth in proximity of the fracture line F.

The absence of the threading 4 in this area allows the development of micro-movements and facilitates the correct formation of the bone callus during the after operation period.

Figure 2:
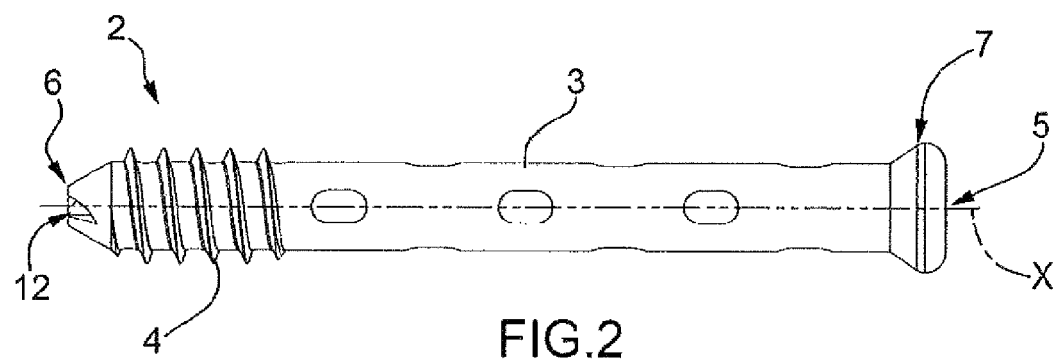
FIG. 2 is a lateral view of a component of the device for selective biological synthesis of a bone tissue according to FIG. 1.
Figure 3:
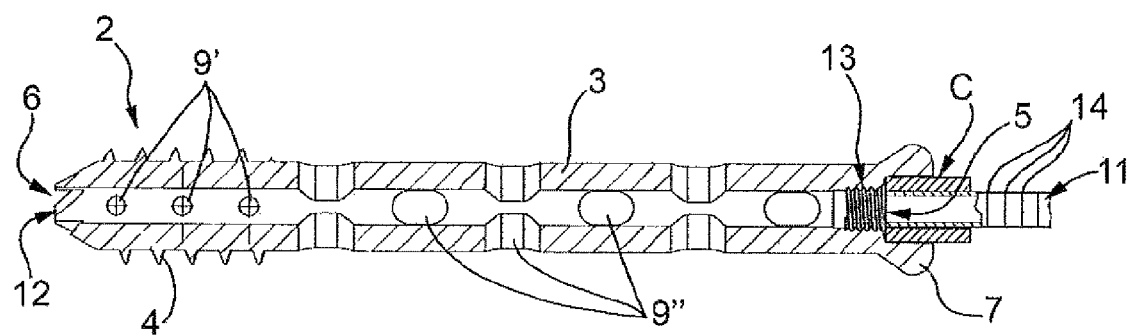
FIG. 3 is a sectional lateral view of some components of the device for selective biological synthesis of a bone tissue according to FIGS. 1 and 2.

As observable in FIGS. 1-3, the screw 2 has, in the extended body 3 thereof, a series of through holes or slots 9, in communication with the longitudinal channel 5 and arranged so as to allow the selective injection of the bone cement and/or the aforementioned substances through the desired holes or slots 9. In particular, the holes or slots 9 comprise various shapes, positions and dimensions, so as to allow a "targeted" introduction of the aforementioned substances into the required and/or desired positions, as specified hereinafter. Actually, a further object of the present invention is to provide a device for selective biological synthesis of a bone tissue capable of allowing the accurate introduction of fluids so as to direct them into the site of greater need/use.

Figure 6:
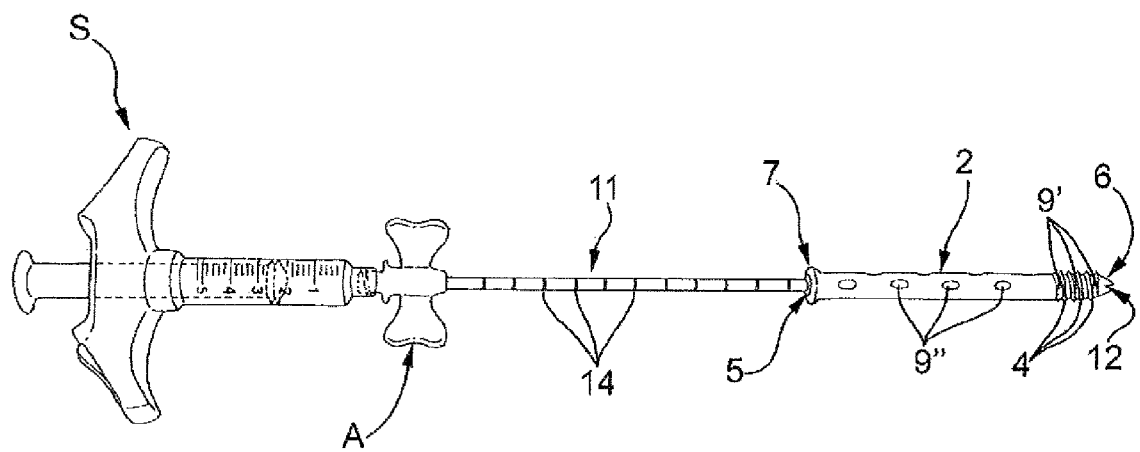
FIG. 6 is a top view of the device for selective biological synthesis of a bone tissue completely assembled according to the present invention.
Figure 7:
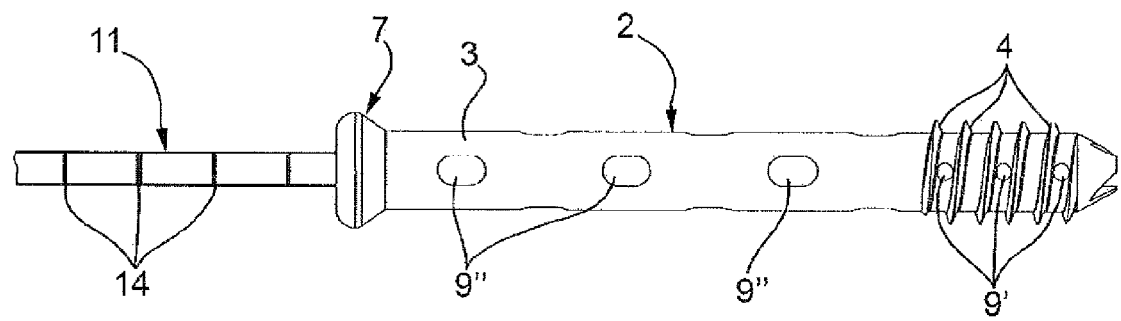
FIG. 7 is an enlarged view of a detail of FIG. 6.

In a particular embodiment, illustrated in FIGS. 3 and 6-7, the holes or slots 9 comprise: circular holes 9', arranged between the turns of the threading 4 and adapted to guarantee a homogeneous distribution of the substances, and elliptic holes 9", arranged in polar position alternated at 360° along the extended body 3 and adapted to guarantee high flow rate.

In particular, the circular holes 9' do not have an identical position along the axis X of the screw 2 but they have a helical development, given that they follow the development of the threading 4. They are small in dimension but approached with respect to each other, so as to guarantee the required capacity and diffusion of the previously indicated substances.

The elliptic holes 9", instead have larger dimensions with respect to those of the circular holes 9', and thus greater flow rate. The elliptic shape is conferred to prevent possible weakening of the structure of the screw 2, which could be created, for example, by circular holes of the same flow rate as the elliptic holes 9".

The holes 9 are arranged substantially along the entire surface of the extended body 3 of the screw 2, so as to have the possibility of performing, through the screw 2, selective injection of the previously mentioned substances at any desired or required position.

Figure 4:
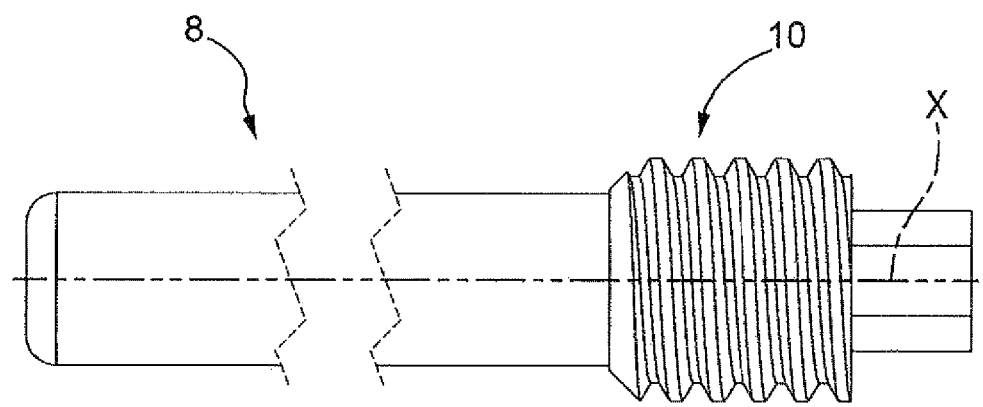
FIG. 4 is an interrupted lateral view of a further component of the device for selective biological synthesis of a bone tissue according to the present invention.
Figure 5:
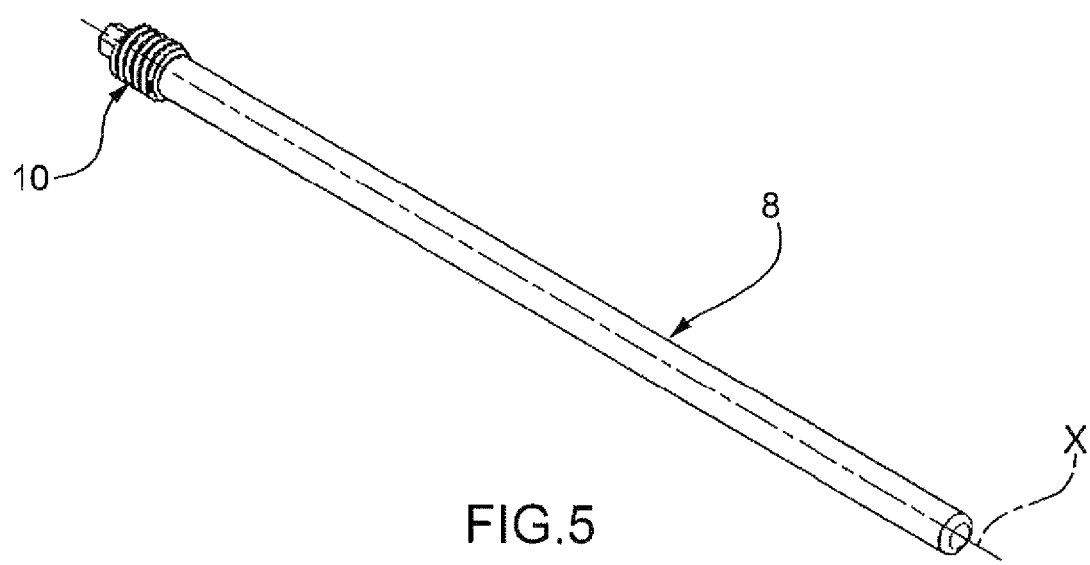
FIG. 5 is a perspective view of the further component of the device for selective biological synthesis of a bone tissue according to FIG. 4.

However, such positions and arrangement of the holes or slots 9 represent an exemplifying but non-limiting characteristic of the present invention. As observable in FIGS. 4 and 5, the device for selective biological synthesis of a bone tissue further comprises a pin 8, having a substantially extended configuration and parallel to the axis X of the screw 2, adapted to guarantee greater resistance of the implant.

The pin 8 has a first distal end, arranged at the first end or tip 6 of the screw 2, and a second proximal end, arranged at the second end or head 7 of the screw 2.

The pin 8 has a length substantially equivalent to that of the longitudinal channel 5. The pin 8 is inserted into the longitudinal channel 5 of the screw 2, at the end of the injection of the previously indicated substances, by means of a special insertion tool, possibly in form of a screwdriver. The insertion of the pin 8 in the longitudinal channel 5 determines the emptying of the latter of the bone cement and/or of the injected substances. This allows obtaining an accurate measurement of the amount of cement and/or injected substances given that the amount measured by the injection system S corresponds to that actually injected into the insertion site of the screw 2.

Furthermore, the emptying of the longitudinal channel 5 by the pin 8 allows making the channel available for possible further injection of substances or for the subsequent prescribed surgical operation.

The diameter of the pin 8 is slightly smaller than the diameter of the longitudinal channel 5 into which it is inserted but such to allow closure thereof.

Due to the bending forces, the outer screw deforms and the two ends of the screw rest on the inner pin 8 and thus, though the pin 8 is not completely integrated in the tubular region, it however contributes to the resistance of the device 1.

In particular the pin 8 has a snap-fitting constraint in the proximal end thereof, at the releasable connection means, as better described hereinafter, and a slidable support in the other distal end.

The pin 8 is made of titanium or the alloys thereof. The resistance thus obtained is greater than any cannulated screw present in the prior art.

Actually, the introduction of the pin 8 guarantees the closure of the screw 2 and further reinforces the resistance of the device 1, transforming a cannulated section, such as the screw 2, into a solid section, provided by the spin 8 inserted into the screw 2, and partly eliminating the effects of the groove given by the presence of holes or slots 9.

The pin 8 can be inserted and/or screwed into the longitudinal channel 5 and there are provided releasable connection means for such purpose.

Such releasable connection means are arranged at the proximal end thereof or at any other point of the pin 8 suitable for the purpose. Such releasable connection means allow the pin 8 to be reversibly connected to the screw 2, due to the presence on the latter, of corresponding releasable means positioned in proximity of the second end or head 7 of the screw 2 or however at said releasable connection means of the pin 8.

The releasable connection means, in a first embodiment, are constituted by a threading 10, present at the proximal end of the pin, and, as observable in FIG. 3, by a female screw 13 positioned at the second end or head 7 of the screw 2, into which there is screwed the threading 10 of the pin 8.

In a further embodiment, the releasable connection means may acquire a bayonet configuration or any other known type of reversible coupling.

The pin 8 has a section corresponding to the section of the longitudinal channel 5 of the screw 2 into which it is inserted.

The technique that can be used for the plant of the device 1 comprises the following steps: inserting a guide wire, preparing the intervention seat on the cortical part of the bone by mounting a mill on the guide wire, extracting the mill and reducing the fracture. Subsequently, the implant technique provides for the following steps: mounting a measuring device on the guide wire, so as to identify the correct length of the screw 2. Then the screw 2 is mounted on a special first insertion tool, for example a screwdriver or other tools suitable for the purpose, mounting the first insertion tool and the screw 2 on the guide wire and the ensuing screwing thereof, by rotating the insertion tool.

Such insertion tool has a handle, a hollow rod C, adapted to allow the passage of the guide wire therein and other devices and/or accessories required in the subsequent steps of the implant, and a tip complementary to the coupling element present in the second end or head 7 of the screw 2, so as to allow screwing thereof.

Upon inserting and/or screwing the screw 2, the guide wire is extracted, just like the handle of the first insertion tool. The rod C of the first insertion tool, is instead left in the seat for a subsequent use thereof.

In a subsequent step there occurs the preparation and mounting the injection system S, possibly in form of a syringe, into which there are inserted the previously indicated substances such as: bone cement and/or regenerative factors and/or stem cells and/or growth factors and/or platelet gel and/or other antibiotic or medicinal substances, etcetera.

The device 1 further comprises an injector 11, of the cannulated type, comprising a lower end, adapted to be coupled with the injection system S, possibly by means of an adapter A of the known type, and an upper end, through which the aforementioned substances are injected, adapted to be inserted into the longitudinal channel 5 of the screw 2.

The injector 11 allows obtaining a selective injection of the abovementioned substances through the required/desired holes or slots 9 and/or through the first end or tip 6 of the screw 2. Such injector 11 is inserted into the longitudinal channel 5 of the screw 2; such injector 11 may be completely inserted into the longitudinal channel 5 of the screw 2, allowing reaching the portions of the screw 2 corresponding to the first end or tip thereof. This allows bringing the material or the substances that should be inserted into the screw 2 in proximity of the desired points, preventing the substance or the material that should be injected through the screw 2, being in fluid state, from being dispersed in undesired and non-required points.

In a first embodiment, the insertion of the injector 11 into the longitudinal channel 5 allows reaching, and thus spreading, first the distal part of the screw 2, at the end or tip 6 thereof, and then the cylindrical holes 9', that would be otherwise difficult to reach by the substances introduced into the screw 2, and secondly the elliptic holes 9".

In a further embodiment, the possibility of inserting the injector 11 into longitudinal channel 5 allows reaching given and specific holes 9 and thus performing a selective injection solely in some holes or performing injection of determined substances in some holes and other substances in other holes, depending on the needs of the patient. In particular, in an exemplifying and non-limiting embodiment, it would be possible to perfuse with bone cement the holes corresponding to the ends 6 and 7 of the screw 2, with the aim of anchoring them into the insertion site. It would thus be possible perfuse with regenerative substances or substances of any other type the holes at the fracture line where, in some cases, it would be advisable to avoid perfusion of the bone cement and where instead it is possible to introduce regenerative substances, with the aim of promoting bone regeneration and the ensuing consolidation of the fracture. Also other injection variants can be provided for, depending on the therapeutic approach and the conditions of the patient.

The selective injection described above is carried out in an accurate and efficient manner given that the injector 11 has a series of graduated references 14, which allow alignment thereof with the base of the first insertion tool and then with the tip 6 of the screw 2. Such references allow identifying and reaching the desired or required holes or slots 9. After inserting the injector 11 on the previously filled injection system and before inserting the injector 11 into the rod C of the insertion tool, there follows the filling of the injector with the substances contained in the injection system S.

At the upper end of the injector 11 there is inserted, possibly, a protection against the reflux (not illustrated) which prevents the insertion and the raising of the biological fluid or any other type of fluid in the injector 11.

Upon inserting the injector 11 into the rod C of the insertion tool, there occurs the alignment of the graduated references 14 of the injector 11, and hence of the upper end thereof with the base of the insertion tool, so as to identify and select the position of the various holes or slots 9 to be subjected to perfusion, depending on the depth intended to be reached with the upper end of the injector or the operation strategy being followed. Obtaining homogeneous injection along the entire extended body 3 of the screw 2 requires starting the injection from the distal part of the screw 2, at the first end or tip 6 thereof.

Upon terminating the injection in the desired points, the implantation technique provides for detaching the injection system S from the injector 11, still in the site, and inserting, into the injector, an emptying device (not illustrated), so as to entirely empty the body of the injector 11 and prevent the loss of bone cement and/or regenerative factors and/or other substances in the soft tissues or in the rod C of the first insertion tool.

The emptying device is in form of a plunger or pin or any other form suitable for the purpose.

Upon extracting the injector 11 alongside the emptying device, the pin 8 is mounted in a special second insertion tool and the entirety is inserted into the first insertion tool left in the seat. The pin 8 is inserted and/or screwed by rotating the second insertion tool coupling the releasable coupling means arranged at the proximal end of the pin and the second end or head 7 of the screw 2.

Once the pin 8 is inserted and/or screwed, there are extracted the first and the second insertion tool. Due to the insertion of the pin 8, the screw 2 is left clear of bone cement residues and/or other substances and this allows—during check-up—to remove the pin 8 and perform new injection operations if required or periodical therapeutic strategy check-ups through repeatable, selective and minimally traumatic surgical operations. The screw 2 thus has a releasable closure by the pin 8.

Thus, the presence of the pin 8 which clears the longitudinal channel 5 and the releasable connection means, allows obtaining an injection of the substances indicated above deferred over time, besides being selective.

During the intervention it is advisable to implant at least two screws with parallel direction, one upper and one lower, with a distance of about 17 mm from each other, to improve the overall resistance of the device 1 on the bone and to prevent, in the absence of the second screw, the rotation of the detached bone segment on the axis of the first.

The present invention further comprises a method for selective biological synthesis of a bone tissue, the stabilization of bone fractures, the spread, in the bone tissue, of biological substances and/or bone cement useful for the primary stabilization and/or regeneration of the bone tissue, according the steps of providing the screw 2, providing an injection system S for the injection of the bone cement and/or regenerative factors and/or stem cells and/or growth factors and/or platelet gel and/or other antibiotic or medicinal substances, providing an injector 11, comprising a lower end, adapted to be coupled with the injection system S, and an upper end, through which the aforementioned substances are injected, adapted to be inserted into the longitudinal channel 5 of the screw 2, by inserting the injector 11 into the longitudinal channel 5.

The method according to the invention comprises a further step of aligning the injector 11, through a series of graduated references 14 present thereof, with the first end or tip 6 of the screw 2.

Furthermore, there are provided the steps of displacing, slidably, the proximal end of the injector 11 to align it with the selected holes or slots 9, for injecting the aforementioned substances through the screw 2 and/or selected holes 9.

The method according to the invention further comprises the steps of extracting the injector 11, providing a pin 8, inserting the pin 8 into the longitudinal channel 5, reversibly fastening the screw 2 through releasable connection means provided for on the pin 8 with ensuing emptying of the longitudinal channel 5.

Regarding the method according to the present invention, there are further steps of disconnecting the pin 8 from the screw 2, repeating the step of injecting, the aforementioned substances by means of the injector 11, through the screw 2 and/or holes 9, reinserting, after removing the injector 11, the pin 8 releasably.

The present invention as conceived can be subjected to various modifications and variants all falling within the scope of protection of the claims.

The invention claimed is:

1. A device for selective biological synthesis of a bone tissue comprising:
   a screw for the stabilization of a fracture or of an osteoporotic bone tissue, wherein said screw is arranged along an axis (X), substantially longitudinal with respect to said screw itself, and comprising an extended body, a first end and a second end,
   wherein at least said extended body and said second end comprise a longitudinal channel, wherein said extended body of said screw comprises a portion having a substantially smooth outer surface having a plurality of elliptical holes, and a portion proximate to the first end having external threading and including a plurality of circular holes arranged between turns of said external threading,
   wherein said device comprises a pin, insertable into said longitudinal channel and provided with releasable connection means with said screw, for reinforcing the device and for the releasable closure of the same, and
   wherein said device comprises an injector of the cannulated type, comprising a lower end, suitable to be inserted into an injection system, and an upper end, suitable to be inserted into said longitudinal channel of said screw so as to obtain a selective injection through said circular or elliptical holes.

2. The device according to claim 1, wherein said pin has a substantially extended configuration, parallel to the axis (X) of said screw, and it has with first distal end, arranged at said first end of said screw, and a second proximal end, arranged at said second end of said screw.

3. The device according to claim 1, wherein said pin has a diameter slightly smaller than the diameter of said longitudinal channel and/or a length substantially equivalent to that of said longitudinal channel.

4. The device according to claim 1, wherein said pin is suitable to be inserted into said longitudinal channel by screwing.

5. The device according to claim 1, wherein said pin is made of titanium or alloys thereof.

6. The device according to claim 1, wherein said releasable connection means are arranged at said proximal end of said pin.

7. The device according to claim 1, wherein said releasable connection means comprise a threading, present on said pin, and a female screw positioned at said second end or head or connection means of bayonet configuration or any other known type of reversible coupling.

8. The device according to claim 1, wherein said reinforcing made by said pin gives a greater resistance to said device.

9. The device according to claim 1, wherein said pin has a snap-fitting constraint in the proximal end thereof, at said releasable connection means, and a slidable support in the other distal end.

10. The device according to claim 1, wherein said first end is substantially tapered and/or has a shape suitable to allow the insertion of said screw into the body of a patient.

11. The device according to claim 1, wherein said screw is configured to form a nail or any other means suitable for the purpose and has a cylindrical section, prismatic section or any other section capable of facilitating insertion thereof into the body of a patient.

12. The device according to claim 1, wherein said lower end is suitable to be inserted into said injection system through adaptor means of the known type.

13. The device according to claim 12, wherein said device allows injection into the concerned site, through said injector and said system for injecting bone cement and/or regenerative factors and/or stem cells and/or growth factors and/or platelet gel and/or other antibiotic or medicinal substances.

14. The device according to claim 12, wherein said circular or elliptical holes comprise holes of various positions and sizes, so as to allow targeted introduction of said bone cement and/or regenerative factors and/or stem cells and/or growth factors and/or platelet gel and/or other antibiotic or medicinal substances, into the required and/or desired positions.

15. The device according to claim 1, wherein said upper end of said injector is inserted into said longitudinal channel of said screw at a position selectable depending on the position of the screw intended to be reached or of said circular or elliptical holes to be subjected to perfusion.

16. The device according to claim 1, wherein said injector has one or more graduated references suitable to refer the upper end of the injector with said circular or elliptical holes or slots.

17. The device according to claim 1, wherein said injector comprises an anti-reflux protection, positionable on said upper end of said injector and/or an emptying device, in form of a plunger or pin, for emptying said injector.

18. A device for selective biological synthesis of a bone tissue comprising:
a screw for the stabilization of a fracture or of an osteoporotic bone tissue, wherein said screw is arranged along an axis (X), substantially longitudinal with respect to said screw itself, and comprising an extended body, a first end and a second end,
wherein at least said extended body and said second end comprise a longitudinal channel, wherein said extended body of said screw comprises a portion having a substantially smooth outer surface having a plurality of elliptical holes, and a portion proximate to the first end having external threading and including a plurality of circular holes arranged between turns of said external threading,
wherein said device comprises a pin, insertable into said longitudinal channel and provided with releasable connection means with said screw, for reinforcing the device and for the releasable closure of the same,
wherein said device comprises an injector of the cannulated type, comprising a lower end, suitable to be inserted into an injection system, and an upper end, suitable to be inserted into said longitudinal channel of said screw so as to obtain a selective injection through said circular or elliptical holes, and
wherein said upper end of said injector is inserted into said longitudinal channel of said screw at a position selectable depending on the position of the screw intended to be reached or of said circular or elliptical holes to be subjected to perfusion.

* * * * *